(12) United States Patent
Tan et al.

(10) Patent No.: US 11,574,741 B2
(45) Date of Patent: Feb. 7, 2023

(54) SYSTEMS AND METHODS FOR DETERMINING CARDIAC OUTPUT

(71) Applicants: Abiomed, Inc., Danvers, MA (US); Massachusetts Institute of Technology, Cambridge, MA (US); The Brigham and Women's Hospital Inc., Boston, MA (US)

(72) Inventors: Qing Tan, Danvers, MA (US); Ahmad El Katerji, Danvers, MA (US); Noam Josephy, Danvers, MA (US); Elazer R. Edelman, Cambridge, MA (US); Brian Yale Chang, Cambridge, MA (US); Steven Keller, Cambridge, MA (US); Sonya Sanat Bhavsar, Danvers, MA (US)

(73) Assignees: Abiomed, Inc., Danvers, MA (US); Massachusetts Institute of Technology, Cambridge, MA (US); The Brigham and Women's Hospital Inc., Boston, MA (US)

( * ) Notice: Subject to any disclaimer, the term of this patent is extended or adjusted under 35 U.S.C. 154(b) by 379 days.

(21) Appl. No.: 16/446,427

(22) Filed: Jun. 19, 2019

(65) Prior Publication Data
US 2020/0146561 A1 May 14, 2020

Related U.S. Application Data

(60) Provisional application No. 62/863,146, filed on Jun. 18, 2019, provisional application No. 62/863,136, (Continued)

(51) Int. Cl.
A61B 5/029 (2006.01)
G16H 50/50 (2018.01)
(Continued)

(52) U.S. Cl.
CPC ........... *G16H 50/50* (2018.01); *A61B 5/0215* (2013.01); *A61B 5/02141* (2013.01); (Continued)

(58) Field of Classification Search
CPC .............................. A61M 60/50; A61M 60/00
See application file for complete search history.

(56) References Cited

U.S. PATENT DOCUMENTS 3,677,092 A  7/1972  Guarino
4,598,579 A  7/1986  Cummings et al.
(Continued)

FOREIGN PATENT DOCUMENTS

WO  97/49439  12/1997
WO  98/43688 A1  10/1998
(Continued)

OTHER PUBLICATIONS

International Search Report PCT/US2017/052259, dated Dec. 19, 2017 (4 pages).
(Continued)

*Primary Examiner* — Alex M Valvis
*Assistant Examiner* — Aurelie H Tu
(74) *Attorney, Agent, or Firm* — Botos Churchill IP Law LLC

(57) ABSTRACT

The systems and methods described herein determine metrics of cardiac or vascular performance, such as cardiac output, and can use the metrics to determine appropriate levels of mechanical circulatory support to be provided to the patient. The systems and methods described determine cardiac performance by determining aortic pressure measurements (or other physiologic measurements) within a single heartbeat or across multiple heartbeats and using such measurements in conjunction with flow estimations or flow measurements made during the single heartbeat or multiple (Continued)

heartbeats to determine the cardiac performance, including determining the cardiac output. By utilizing a mechanical circulatory support system placed within the vasculature, the need to place a separate measurement device within a patient is reduced or eliminated. The system and methods described herein may characterize cardiac performance without altering the operation of the heart pump (e.g., without increasing or decreasing pump speed).

20 Claims, 7 Drawing Sheets

Related U.S. Application Data filed on Jun. 18, 2019, provisional application No. 62/687,133, filed on Jun. 19, 2018.

(51) Int. Cl.

| | |
|---|---|
| *G16H 40/63* | (2018.01) |
| *A61B 5/021* | (2006.01) |
| *A61B 5/0215* | (2006.01) |
| *A61M 60/148* | (2021.01) |
| *A61M 60/411* | (2021.01) |
| *A61M 60/216* | (2021.01) |
| *A61M 60/13* | (2021.01) |
| *A61M 60/523* | (2021.01) |
| *A61M 60/515* | (2021.01) |
| *A61M 60/538* | (2021.01) |
| *A61M 60/531* | (2021.01) |

(52) U.S. Cl.
CPC .......... *A61M 60/13* (2021.01); *A61M 60/148* (2021.01); *A61M 60/216* (2021.01); *A61M 60/411* (2021.01); *A61M 60/515* (2021.01); *A61M 60/523* (2021.01); *A61M 60/531* (2021.01); *A61M 60/538* (2021.01); *G16H 40/63* (2018.01); *A61M 2205/3334* (2013.01); *A61M 2205/3344* (2013.01); *A61M 2230/04* (2013.01)

(56) References Cited

U.S. PATENT DOCUMENTS

| | | | |
|---|---|---|---|
| 4,877,035 | A | 10/1989 | Bogen et al. |
| 5,365,933 | A | 11/1994 | Elghazzawi |
| 5,437,284 | A | 8/1995 | Trimble |
| 6,159,160 | A | 12/2000 | Hsei et al. |
| 6,176,822 | B1 | 1/2001 | Nix et al. |
| 6,234,759 | B1 | 5/2001 | Hennel et al. |
| 6,623,420 | B2 | 9/2003 | Reich et al. |
| 7,010,954 | B2 | 3/2006 | Siess et al. |
| 7,022,100 | B1 | 4/2006 | Aboul-Hosn et al. |
| 8,282,564 | B2 * | 10/2012 | Parlikar ................ A61B 5/021 600/485 |
| 2003/0139643 | A1 | 7/2003 | Smith et al. |
| 2004/0039243 | A1 | 2/2004 | Bearnson et al. |
| 2004/0106874 | A1 | 6/2004 | Eigler et al. |
| 2008/0097226 | A1 | 4/2008 | McConnell |
| 2009/0270739 | A1 | 10/2009 | Hatib et al. |
| 2010/0056931 | A1 | 3/2010 | Soffer et al. |
| 2010/0268333 | A1 | 10/2010 | Gohean et al. |
| 2013/0041204 | A1 * | 2/2013 | Heilman .............. A61M 60/113 600/17 |
| 2013/0046129 | A1 | 2/2013 | Medvedev et al. |
| 2014/0243696 | A1 * | 8/2014 | Peyton .................. A61B 5/029 600/526 |
| 2014/0296615 | A1 | 10/2014 | Franano |
| 2015/0246166 | A1 | 9/2015 | Greatrex et al. |
| 2016/0367740 | A1 | 12/2016 | Aboul-Hosn et al. |
| 2017/0065186 | A1 * | 3/2017 | Joseph ................ A61B 5/6876 |
| 2017/0136164 | A1 | 5/2017 | Yeatts |
| 2017/0239407 | A1 | 8/2017 | Hayward |
| 2018/0078159 | A1 | 3/2018 | Edelman et al. |
| 2018/0146864 | A1 | 5/2018 | Jansen et al. |
| 2021/0052791 | A1 | 2/2021 | Granegger |

FOREIGN PATENT DOCUMENTS

| | | |
|---|---|---|
| WO | 2004/017818 | 3/2004 |
| WO | 2014/062911 | 4/2014 |
| WO | 2017102164 A1 | 6/2017 |
| WO | 2018/036927 | 3/2018 |
| WO | 2018/073150 | 4/2018 |
| WO | 2018/146045 | 8/2018 |

OTHER PUBLICATIONS

International Search Report PCT/US2019/038039, dated Sep. 5, 2019 (6 pages).
International Search Report PCT/US2019/038049, dated Sep. 5, 2019 (6 pages).
PCT International Search Report for PCT/US2018/036757, dated Sep. 10, 2018 (5 pages).
Rüschen et al., "Online cardiac output estimation during transvalvular left ventricular assistance," Computer Methods and Programs in Biomedicine, vol. 171: 87-97 (2019).
Rüschen et al., "Robust Assistance Control of Left Ventricular Assist Devices," IFMBE Proceedings, vol. 65(13): 294-297 (2017).
Sekii et al., "Beat-to-Beat Prediction of Left Ventricular Output During Left Ventricular Bypass Pumping," Proceedings of the Annual International Conference of the IEEE Engineering in Medicine and Biology Society: 10th Annual International Conference—Nov. 4, 1988: 1773-1775.
Stolinski, et al, "The heart-pump interaction: Effects of a microaxial blood pump", International Journal of Artificial Organs, vol. 25, No. 11, pp. 1082-1088 (2002).
Search Report and Written Opinion from corresponding Singapore Application No. 11202012264T dated Aug. 12, 2022 (10 pages).
Office Action from corresponding Indian Application No. 202117001344 dated Sep. 22, 2022 (7 pages).
Search Report issued in corresponding Singapore Patent Application No. 11202012262X dated Jul. 26, 2022, 3 pages,.
Written Opinion issued in corresponding Singapore Patent Application No. 11202012262X dated Aug. 19, 2022, 7 pages.
Examination Report issued in corresponding Indian Patent Application No. 202117001343 dated Oct. 13, 2022, 8 pages.

\* cited by examiner

200

202
Apply hemodynamic support, the hemodynamic support comprising providing a first pumping rate during a plurality of beats of the heart, each beat including a systolic rise, a dicrotic notch, and a diastolic fall that occurs after the dicrotic notch

204
Detect a first aortic pressure measurement at a first time and a second aortic pressure measurement at a second time, wherein the first time and the second time occur during the diastolic fall of a specific beat of the plurality of beats

206
Determine a first rate of blood flow pumped by the intravascular blood pump at the first time and a second rate of blood flow pumped by the intravascular blood pump at the second time

208
Determine cardiac output during the specific beat based on the first aortic pressure measurement, the second aortic pressure measurement, the first rate of blood flow, and the second rate of blood flow.

502
Monitor a Hemodynamic Parameter During Operation of a Heart Pump at a First Pump Speed

504
Identify a Diastolic Period of a Heartbeat Cycle, Based on a Shape of the Hemodynamic Parameter Over Time

506
Establish a Time-variant Relationship Between Aortic Pressure and Blood Flow During the Diastolic Period

508
Calculate, Based on the Time-variant Relationship Between Aortic Pressure and Blood Flow During the Diastolic Period, Total Volume of Blood Pumped per Heartbeat, Which is Representative of Cardiac Performance

SYSTEMS AND METHODS FOR DETERMINING CARDIAC OUTPUT

CROSS-REFERENCE TO RELATED APPLICATIONS

This application claims priority to and the benefit of U.S. Provisional Patent Application No. 62/687,133, filed on Jun. 19, 2018, and entitled "METHODS AND SYSTEMS FOR IMPROVED ASSESSMENT OF VASCULAR AND CARDIAC STATE"; U.S. Provisional Patent Application No. 62/863,136, filed on Jun. 18, 2019, and entitled "SYSTEMS AND METHODS FOR SYSTEM IDENTIFICATION"; and U.S. Provisional Patent Application No. 62/863,146, filed on Jun. 18, 2019, and entitled "SYSTEMS AND METHODS FOR DETERMINING CARDIAC PERFORMANCE". The entire contents of the above-referenced applications are incorporated herein by reference.

BACKGROUND

Cardiovascular diseases are a leading cause of morbidity, mortality, and burden on healthcare around the world. A variety of treatment modalities have been developed for heart health, ranging from pharmaceuticals to mechanical devices and transplantation. Temporary cardiac support devices, such as heart pump systems, provide hemodynamic support, and facilitate heart recovery. Some heart pump systems are percutaneously inserted into the heart and can run in parallel with the native heart to supplement cardiac output, such as the IMPELLA® family of devices (Abiomed, Inc., Danvers Mass.). Such heart pump systems may measure and/or calculate heart pump parameters useful for determining patient health and judging operation of the heart pump system. The pump may be positioned across the heart's aortic valve such that a blood inlet to the pump is within the left ventricle and an outlet from the pump is within the aorta. In some implementations, the pump is positioned within the right ventricle of the heart. If the pump is positioned across the aortic valve such that a blood inlet to the pump is within the left ventricle and an outlet from the pump is within the aorta, the pump contributes to native heart operation by unloading the left ventricle.

The cardiac support, as measured by the volumetric flow of blood delivered by the pumping device, or the duration of cardiac support that each patient needs can vary. It is difficult for clinicians to directly and quantitatively determine how much support a device should deliver or when to terminate use of a heart pump system, particularly for patients who recover from intervention or other cardiac care. Thus, clinicians tend to rely on judgments and indirect estimates of cardiac function, such as measuring intracardiac or intravascular pressures using fluid filled catheters. Cardiac output (CO) in particular is difficult to quantify. Pulmonary artery catheters (PAC) may provide real-time measures of central venous pressure and pulmonary artery pressure, and may estimate CO using Fick's laws through measures of systemic oxygen consumption or the bolus thermodilution method. Because of the assumptions that must be made to arrive at CO metrics and the corresponding lack of fidelity with more invasive metrics, PACs have been unable to establish reliable association with clinical outcomes. Measurements through PACs discount dynamic changes in cardiac function and are not continuous, while non-linear aspects of systemic ventricular vascular coupling are not adequately captured.

SUMMARY

The systems and methods described herein determine metrics of cardiac performance, such as CO, for a single heartbeat of a patient, and can use the metrics to determine appropriate levels of mechanical circulatory support to be provided to the patient. The cardiac performance metrics can be measured in multiple beats and processed mathematically to arrive at a model for the performance of that patient's heart in general. The determinations can be done using a mechanical circulatory support system, such as an intravascular blood pump system. The systems and methods characterize cardiac performance from pressure and flow measurements or estimations of pressure and flow during use of the mechanical circulatory support system, as determined within the period of a single heartbeat of one or more heartbeats. The systems and methods described herein may be readily validated and utilized in clinical applications because they utilize existing measurements acquired by the mechanical circulatory support system. The systems and methods described herein leverage the operation of an indwelling mechanical circulatory support device without the need for additional measurements or catheters to determine CO. The potential to continuously and accurately track changes in systemic vascular resistance and compliance as well as estimate cardiac stroke volume marks a significant advancement over traditional measures obtained from a PAC or other diagnostics readily deployed in clinical practice.

The systems and methods described determine cardiac performance by determining aortic pressure measurements (or other physiologic measurements) within a single heartbeat or across multiple heartbeats and using such measurements in conjunction with flow estimations or flow measurements made during the single heartbeat or multiple heartbeats to determine the cardiac performance, including determining the cardiac output. By utilizing a mechanical circulatory support system placed within the vasculature, the need to place a separate measurement device within a patient is reduced or eliminated. Because measurements may be made within a single heartbeat, the heart's performance within one or more beats may be characterized in a continuous manner from one beat to another—e.g., the heart performance may be measured for each heartbeat in a series of heartbeats. Additionally, the operation of the heart pump is not impaired by the acquisition of these measurements. The system and methods described herein may characterize cardiac performance without altering the operation of the heart pump (e.g., without increasing or decreasing pump speed). This may be particularly beneficial if a patient is entirely reliant on the heart pump's blood flow contribution, such that the speed of the heart pump cannot be decreased without potentially harming the patient, or if other instrumentation (e.g., extracorporeal membrane oxygenation (ECMO) systems) prevent an increase in the heart pump speed. In some applications, the systems and methods described herein are used in conjunction with such other instrumentation. The systems and methods described herein may thus provide continuous measurements of heart performance while also providing appropriate heart support.

Hemodynamic support may be provided to a patient's heart via mechanical circulatory support systems, which may include a blood pump and a hemodynamic parameter may be measured during operation of the blood pump. The blood pump may be an intravascular blood pump, intra-aortic balloon pump, ECMO device, or other blood pump (e.g., the Impella® family of devices from Abiomed Inc in Danvers, Mass. or the TandemHeart® family of devices from CardiacAssist Inc. in Pittsburgh, Pa.). Multiple measurements of the hemodynamic parameter may be acquired during a single heartbeat. For example, multiple measurements (e.g., three, four, five, six, seven, ten, twenty, thirty, one hundred or any suitable number of measurements) may be acquired during the diastolic fall of the heartbeat at different times. If the heart performance is modeled as a mathematical system (e.g., via a Windkessel model), the pressure and rates of blood flow at these different times allow a system of equations to be configured, which may then be solved to determine functional values such as systemic vascular resistance and compliance, which are indicative of cardiac performance. Cardiac output (and other metrics indicative of cardiac and/or vascular performance) may then be calculated from the resistance or compliance values. These calculations are not limited to computing resistance and compliance only once for a single heartbeat— for example, the calculations described herein may include computing resistance and compliance for multiple pressure measurements (or groups of pressure measurements) within a single heartbeat, determining resistance and compliance from those measurements, and then averaging or otherwise processing those resistance and compliance values to determine representative resistance, compliance, or other metric values representative of the overall vasculature or heart health for the single heartbeat. Similar measurements can be made of multiple heartbeats, and used to determine an average or other combined measurement that models the cardiac performance of that patient's heart.

In some aspects, hemodynamic support may be applied or adjusted based on the determined cardiac performance measurements. Hemodynamic support is applied to a patient's heart via an mechanical circulatory support device (MCS). In some implementations, the device is an intravascular blood pump placed within the patient's heart via percutaneous insertion. The MCS may be a surgically implanted device, a left ventricular assist device, a counterpulsation device, an expandable heart pump, an extracorporeal membrane oxygenation device, an intra-aortic balloon pump, or any other suitable device. The pump may be introduced to the patient because the patient is in cardiogenic shock, undergoing coronary intervention, having a heart attack, or otherwise experiencing a decline in heart health. The pump contributes to native heart operation such that the CO from the heart is equal to native CO plus pump output.

Providing hemodynamic support may include operating the intravascular blood pump at a first pumping rate or pump speed. The pumping rate is the speed of operation of the pump and corresponds to the amount of blood flow provided by the pump's operation. In some implementations, the pumping rate may correspond to a speed of rotation of a rotor. For example, the pump speed may be 10,000 RPM, 20,000 RPM, 30,000 RPM, 40,000 RPM, 50,000 RPM, 60,000 RPM, 70,000 RPM, 80,000 RPM, 90,000 RPM, 100,000 RPM, or any suitable speed. A pump speed may correspond to a power level, or P-level, as described below in relation to FIG. 1. For example, the pump speed may be P-1, P-2, P-3, P-4, P-5, P-6, P-7, P-8, or P-9. In some implementations, the pumping rate may instead correspond to the rate at which a chamber of the pump fills up with and releases blood.

In some implementations, the hemodynamic support is provided at the first pumping rate during a plurality of beats of the heart. Each beat includes a systolic rise, a dicrotic notch, and a diastolic fall that occurs after the dicrotic notch. For example, the hemodynamic pumping rate may be provided over two, three, four, ten, twenty, thirty, one hundred, two hundred, or any other suitable number of heartbeats. The dicrotic notch marks the start of diastole, which is the phase of the heartbeat when the heart muscle relaxes and allows the chambers to fill with blood. If the intravascular blood pump is a left heart system, while the blood pump is operating, the only substantial flow out of the patient's left ventricle into the aorta during diastole is the flow contributed by the blood pump. The diastolic period is the time for a heart to complete diastole—the phase of the heartbeat when the heart muscle relaxes and allows the chambers to fill with blood. For example, the diastolic period may be 0.05 seconds, 0.1 seconds, 0.2 seconds, 0.3 seconds, 0.4 seconds, 0.5 seconds, 0.6 seconds, 0.7 seconds, 0.8 seconds, 0.9 seconds, 1 second or any suitable length of time.

In some implementations, a hemodynamic parameter is measured to monitor the positioning and performance of the device, as well as the well-being of the patient while on the device. For example, the hemodynamic parameter may be measured with a sensor included in the intravascular blood pump, or may be measured by a separate device. A hemodynamic parameter may be any parameter relating to the flow of blood within the organs and tissues of the body. For example, the hemodynamic parameter may include at least one or more of heart rate, blood pressure, arterial oxygen saturation, mixed venous saturation, central venous oxygen saturation, arterial blood pressure, mean arterial pressure, right arterial pressure, central venous pressure, right ventricular pressure, pulmonary artery pressure, mean pulmonary artery pressure, pulmonary artery occlusion pressure, left atrial pressure, aortic pressure, differential pressure, left ventricular end pressure, stroke volume, stroke volume index, stroke volume variation, systemic vascular resistance, systemic vascular resistance index, pulmonary vascular resistance, pulmonary vascular resistance index, pulmonary vascular resistance, pulmonary vascular resistance index, left ventricular stroke work, left ventricular stoke work index, right ventricular stroke work, right ventricular stroke work index, coronary artery perfusion pressure, right ventricular end diastolic volume, right ventricular end diastolic volume index, right ventricular end systolic volume, right ventricular ejection fraction, arterial oxygen content, venous oxygen content, arterial-venous oxygen content difference, oxygen delivery, oxygen delivery index, oxygen consumption, oxygen consumption index, oxygen extraction fraction, oxygen extraction index, total peripheral resistance, CO, cardiac index, and CPO.

In some implementations, the hemodynamic parameter is aortic pressure. Multiple aortic pressure measurements may be made at respective different times and the results used to detect the location and performance of the pump, and to configure the pump for operation. In some implementations, three or more aortic pressure measurements are detected, all may be within the diastole of the same heartbeat of the plurality of beats or during different beats or times. If the blood pump is a left heart system, the pressure measurements may be optimal during diastole because the only substantial flow through the aorta during diastole is contributed by the blood pump. So determination of pump performance and its contribution to the heart may be easier then.

In some implementations, at least three rates of blood flow pumped by the intravascular blood pump are determined at respective three different times. The flow output from the pump ($i_p$) can be determined by the speed of the pump (rotations per minute or RPM) and the motor current supplied to the pump to maintain that pump speed. The technical relationship between pump speed and motor current allows estimation of flow by mathematical correlation or a look-up table, where the pump speed and motor current are indices to the look-up table. The flow values in the look-up table may be pre-populated through bench testing. Another way to determine flow output from the pump is to determine flow for a sub-set of possible combinations of pump speed and motor current values before placing the pump (or a similar pump) in a patient. For example, if the flow at a pump speed of 40,000 RPM and a motor current of 500 mA is represented by $i_1$ and the flow at a pump speed of 40,000 RPM and motor current of a 510 mA is represented by $i_2$, the flow at pump speed of 40,000 RPM and motor current of 505 mA can be calculated by taking the average of $i_1$ and $i_2$.

CO is determined based on multiple aortic pressure measurements and rates of blood flow. Some adaptations use at least three aortic pressure measurements and at least three corresponding rates of blood flow. In an example, a Windkessel model is used to simulate the vascular system, with two current sources, $i_h$ and $i_p$ in parallel with each other and with a resistance R and compliance C. The governing equation for technical relationship reflected in this model is:

$$C\frac{dP}{dt} + \frac{P}{R} = i_h + i_p \qquad (1)$$

where C is compliance, P is pressure, R is systemic vascular resistance, $i_h$ is flow from native heart operation and $i_p$ is flow from the pump. During diastole, the aortic valve is closed, so the only flow through the left ventricle is from the pump positioned across the valve. By discounting the heart current source and assuming pump flow is constant, the model can thus be simplified as follows:

$$P = P_0 e^{-\frac{t}{RC}} + i_p R \qquad (2)$$

where $P_0$ is a scaling factor of the exponential decay term $$\left(P_0 e^{-\frac{t}{RC}}\right)$$

of the diastolic pressure. For example, the scaling factor $P_0$ may be proportional to the reciprocal of a corresponding pump speed, such that $$\frac{P_{01}}{speed_2} = \frac{P_{02}}{speed_1},$$

where $P_{01}$ is the scaling factor at a first pump speed $speed_1$ and $P_{02}$ is the scaling factor at a second pump speed $speed_2$. Thus, once $P_{0x}$ has been clinically determined for a single pump speed x, the scaling factor $P_{0x}$ may be extrapolated for a range of pump speeds. In some implementations, flow from the pump $i_p$ is estimated from current flow to the motor of the heart pump system to maintain constant speed. Pressure P may be measured at a variety of points within a single diastolic period to characterize and deconstruct the pressure waveform. For example, pressure may be known (e.g., measured) at multiple times and, in the case of the Winkessel model, at three different times. Flow $i_p$ may be estimated at the same times as the pressure measurements. Setting up multiple pressure equations, one each for the times pressure is measured, based on Equation (2), R and C values may be calculated. In some implementations, the heart pump is operated at a constant speed.

Systemic vascular resistance and compliance values may be used to calculate other metrics indicative of heart performance. For example, once R and C have been determined using the Windkessel model described above, CO for the heart may be determined by inserting the calculated R and C values into Equation (1) above and solving for in to determine volumetric flow contributed by native heart function. CO may be calculated by taking the average of the total cardiac flow ($i_h+i_p$) over a desired period of time (e.g., 5 seconds, 10 seconds, 30 seconds, etc.).

In some implementations, other metrics indicative of cardiac performance may be determined. For example, the metric indicative of cardiac performance may be ventricular resistance, ventricular compliance, CO, CPO, stroke volume, stroke work, ejection fraction, cardiac index, or a prediction of patient survival. Many metrics indicative of cardiac performance are interrelated. For example, CO is determined based on the flow rate of the blood through and past the pump. The stroke volume is an index of left ventricular function which formula SV=CO/HR, where SV is the stroke volume, CO is the cardiac output, and HR is the heart rate. Stroke work is the work done by the ventricle to eject a volume of blood and can be calculated from the stroke volume according to the equation SW=SV*MAP, where SW is the stroke work, SV is the stroke volume, and MAP is the mean arterial pressure. Cardiac work is calculated by the product of stroke work and heart rate. CPO is a measure of the heart function representing cardiac pumping ability in Watts. CPO is calculated using the equation CPO=mAoP*CO/451, where CPO is the cardiac power output, mAoP is the mean aortic pressure, CO is the cardiac output, and 451 is a constant used to convert mmHg×L/min into Watts. The ejection fraction can be calculated by dividing the stroke volume by the volume of blood in the ventricle. Other parameters, such as chamber pressure, preload state, afterload state, heart recovery, flow load state, variable volume load state, and/or heartbeat cycle flow state can be calculated from these values or determined via these parameters.

Operation of the pump may be adjusted based on the metric indicative of cardiac performance. Adjusting pump operation may include increasing pump speed, decreasing pump speed, adjusting pump placement, turning the pump off, or any other suitable adjustment. For example, if total volume of blood pumped is below a threshold, the pump speed may be increased, while if the blood volume is above a threshold, the pump speed may be decreased.

In some implementations, a plurality of aortic pressure measurements are detected during the diastolic fall during a specific beat of the plurality of beats. For example, pressure may be sampled at a rate of 1, 2, 3, 10, 20, 30, 100, 200, 300, 1000, 2000, 3000, or any other suitable number of samples per second. In some examples, aortic pressure is only sampled during the diastolic fall. In some examples, aortic pressure is constantly or periodically measured. In some examples, the sampling rate of aortic pressure is altered during the diastolic fall. In some implementations, at least one aortic pressure measurement is taken at the end of diastole, when the cardiac output occurs solely by the operation of a blood pump. In some implementations, the plurality of aortic pressure measurements may be acquired via a pressure sensor. For example, the pressure sensor may be part of an intravascular blood pump providing hemodynamic support to the heart, or the pressure sensor may be separate from the intravascular blood pump.

In some implementations, determining cardiac output for a patient's heart includes processing multiple cardiac output values for a single heartbeat or several heartbeats. For example, as described above, a plurality of aortic pressure measurements may be acquired during diastole of a specific heartbeat. For each pressure measurement in the plurality of aortic pressure measurements, pressure may be measured and flow may be estimated. The pressure and flow values, in combination with the known time of measurement, may be compared between two times to calculate heart parameters such as vascular resistance and compliance and then used to determine CO. Even within a single heartbeat, the calculated CO values across the diastolic fall may vary due to fluctuations in the patient's heart and differences in flow estimation. Processing the plurality of CO values may include performing at least one of a summation, average, or linear regression on the determined plurality of cardiac output values to calculate a first cumulative indicator of cardiac output of the heart. By processing a plurality of CO values for a plurality of aortic pressure measurements in a single heart, the systems and methods described herein provide an accurate representation of CO (and heart performance) for a heart. In some implementations, the first cumulative indicator of cardiac output of the heart is indicative of cardiac performance or overall patient health during the specific heartbeat.

In some implementations, the systems and methods herein may determine cardiac performance by computing CO for multiple heartbeats, and the measurements and determinations of CO can be assessed to identify a cumulative indicator of cardiac performance of the heart. In some implementations, a second cumulative indicator of cardiac output of the heart is determined for a second heartbeat after the specific heartbeat discussed above—i.e., the first cumulative indicator of cardiac output may be representative of a first heartbeat at a first time and the second cumulative cardiac output may be representative of a second heartbeat at a second time later than the first time. In some implementations, the second heartbeat is directly after the first heartbeat. In some implementations, a period of time elapses between the end of the first heartbeat and the start of the second heartbeat. The period of time may be 1 second, 1 minute, 10 minutes, 1 hour, 10 hours, or any other suitable length of time. For example, the first cumulative indicator may be calculated for a heartbeat starting at time 12:00 PM, and the second cumulative indicated may be calculated for a heartbeat starting at 1:00 PM that same day. Investigating the cardiac output of heartbeats at different points in time may allow a clinician or computer system to find overall trends in patient health.

In some implementations, the first cumulative indicator of cardiac output is compared to the second cumulative indicator of cardiac output. Similar to the first cumulative indicator described above, the second cumulative indicator may be determined by calculating a second plurality of cardiac output values, wherein each cardiac output value of the second plurality of cardiac output values corresponds to a beat of the second set of beats. A summation, average, or linear regression is applied to the determined plurality of cardiac output values to calculate the second cumulative indicator, which may be indicative of the overall cardiac performance of the patient's heart.

Based on the comparison between the first cumulative indicator and the second cumulative indicator, either (i) an increase in cardiac performance of the heart or (ii) a decrease in cardiac performance of the heart is determined. The increase or decrease in cardiac performance may be indicative of a patient's cardiac or overall health. Similarly, CO values may be determined for a plurality of heartbeats for the patient and may be used to track cardiac performance over time. The hemodynamic support provided to the patient may be adjusted based on determining whether cardiac performance of the heart is increasing or decreasing over time. That indicator may be used to identify when to apply or adjust mechanical circulatory support levels, and to what extent. In some implementations, if an increase in cardiac performance is observed, the hemodynamic support provided to the patient may be decreased; but if a decrease in cardiac performance is observed, the hemodynamic support provided to the patient may be increased.

In some aspects, a hemodynamic parameter is monitored during operation of a heart pump at a first pump speed. In some implementations, the pump is an intravascular blood pump device placed within the patient's heart via percutaneous insertion. The pump may be introduced to the patient because the patient is in cardiogenic shock or otherwise experiencing a decline in health. The pump may be positioned across the aortic valve such that a blood inlet (e.g., blood inlet 172 of FIG. 1) to the pump is within the left ventricle and an outlet (e.g., outlet openings 170 of FIG. 1) from the pump is within the aorta. The pump contributes with native heart operation such that CO from the heart is equal to native CO plus pump output.

A hemodynamic parameter may be any parameter relating to the flow of blood within the organs and tissues of the body. For example, the hemodynamic parameter may include at least one of heart rate, blood pressure, arterial oxygen saturation, mixed venous saturation, central venous oxygen saturation, arterial blood pressure, mean arterial pressure, right arterial pressure, central venous pressure, right ventricular pressure, pulmonary artery pressure, mean pulmonary artery pressure, pulmonary artery occlusion pressure, left atrial pressure, aortic pressure, differential pressure, left ventricular end pressure, stroke volume, stroke volume index, stroke volume variation, systemic vascular resistance, systemic vascular resistance index, pulmonary vascular resistance, pulmonary vascular resistance index, pulmonary vascular resistance, pulmonary vascular resistance index, left ventricular stroke work, left ventricular stoke work index, right ventricular stroke work, right ventricular stroke work index, coronary artery perfusion pressure, right ventricular end diastolic volume, right ventricular end diastolic volume index, right ventricular end systolic volume, right ventricular ejection fraction, arterial oxygen content, venous oxygen content, arterial-venous oxygen content difference, oxygen delivery, oxygen delivery index, oxygen consumption, oxygen consumption index, oxygen extraction ration, oxygen extraction index, total peripheral resistance, CO, cardiac index, and cardiac power output (CPO). A pump speed is the speed of operation of the pump and corresponds to the amount of blood flow provided by the pump's operation. In some implementations, the pump speed may correspond to a speed of rotation of a rotor. For example, the pump speed may be 10,000 RPM, 20,000 RPM, 30,000 RPM, 40,000 RPM, 50,000 RPM, 60,000 RPM, 70,000 RPM, 80,000 RPM, 90,000 RPM, 100,000 RPM, or any suitable speed. A pump speed may correspond to a power level, or P-level, as described above in relation to FIG. 1. For example, the pump speed may be P-1, P-2, P-3, P-4, P-5, P-6, P-7, P-8, P-9, or any other suitable value. In some implementations, the pump speed may instead correspond to the rate at which a chamber of the pump fills up with and releases blood. By monitoring a hemodynamic parameter, the systems and methods described herein may investigate changes in that hemodynamic parameter over time. Such comparisons may be used to quantify heart performance.

In some implementations, a diastolic period of a heartbeat cycle is identified, based on a shape of the hemodynamic parameter over time. In particular, the dicrotic notch (evident in an aortic pressure waveform, e.g., notch 310 of FIG. 3) indicates the start of diastole. If the patient's heart rate is relatively steady, the start of a heartbeat may be accurate predicted. As the heartbeat completes systole, the aortic pressure decreases before increasing to form the dicrotic notch. Identifying this waveform shape allows the system to determine the start of diastole. The diastolic period is the time for a heart to complete diastole—the phase of the heartbeat when the heart muscle relaxes and allows the chambers to fill with blood. For example, the diastolic period may be 0.05 seconds, 0.1 seconds, 0.2 seconds, 0.3 seconds, 0.4 seconds, 0.5 seconds, 0.6 seconds, 0.7 seconds, 0.8 seconds, 0.9 seconds, 1 second or any suitable length of time.

In some implementations, a time-variant relationship between aortic pressure and blood flow during the diastolic period is determined. The time-variant relationship may be a Windkessel model with two current sources, $i_h$ and $i_p$ in parallel with each other and with a resistance R and compliance C. The governing equation for this model is:

$$C\frac{dP}{dt} + \frac{P}{R} = i_h + i_p \quad (1)$$

where C is compliance, P is pressure, R is vascular resistance, $i_h$ is flow from native heart operation and $i_p$ is flow from the pump. During diastole, however, the aortic valve is closed, so the only flow through the left ventricle is from the pump positioned across the valve. By discounting the heart current source and assuming pump flow is constant, the model can thus be simplified as follows:

$$P = P_0 e^{-\frac{t}{RC}} + i_p R \quad (2)$$

where $P_0$ is the scaling factor of the exponential decay part of the diastolic pressure. In some implementations, flow from the pump $i_p$ is estimated from current flow to the motor of the heart pump system to maintain constant speed. Pressure P may be measured at a variety of points within a single diastolic period to characterize and deconstruct the pressure waveform. For example, pressure may be known at a first, second, and third time. Flow $i_p$ may be estimated at the first, second and third time as well. Setting up three pressure equations, one each for the three times respectively, based on Equation (2), R and C values may be calculated. In some implementations, the heart pump is operated at a constant speed.

In some implementations, a total volume of blood pumped per heartbeat, which is representative of cardiac performance, is calculated based on the time-variant relationship between the aortic pressure and blood flow during the diastolic period. For example, once R and C have been determined, CO for the heart may be determined by plugging the calculated R and C values into Equation (1) above and solving for $i_h$ to determine volumetric flow contributed by native heart function.

In some implementations, other metrics indicative of cardiac performance may be computed. For example, the metric indicative of cardiac performance may be ventricular resistance, ventricular compliance, CO, CPO, stroke volume, stroke work, ejection fraction, cardiac index, or a prediction of patient survival. Many metrics indicative of cardiac performance are interrelated. For example, CO is determined based on the flow rate of the blood through and past the pump. The stroke volume is an index of left ventricular function which formula SV=CO/HR, where SV is the stroke volume, CO is the cardiac output, and HR is the heart rate. Stroke work is the work done by the ventricle to eject a volume of blood and can be calculated from the stroke volume according to the equation SW=SV*MAP, where SW is the stroke work, SV is the stroke volume, and MAP is the mean arterial pressure. Cardiac work is calculated by the product of stroke work and heart rate. CPO is a measure of the heart function representing cardiac pumping ability in Watts. CPO is calculated using the equation CPO=mAoP*CO/451, where CPO is the cardiac power output, mAoP is the mean aortic pressure, CO is the cardiac output, and 451 is a constant used to convert mmHg×L/min into Watts. The ejection fraction can be calculated by dividing the stroke volume by the volume of blood in the ventricle. Other parameters, such as chamber pressure, preload state, afterload state, heart recovery, flow load state, variable volume load state, and/or heartbeat cycle flow state can be calculated from these values or determined via these parameters.

In some implementations, operation of the pump is adjusted, based on the metric indicative of cardiac performance. Adjusting pump operation may include increasing pump speed, decreasing pump speed, adjusting pump placement, turning the pump off, or any other suitable adjustment. For example, if total volume of blood pumped is below a threshold, the pump speed may be increased, while if the blood volume is above a threshold, the pump speed may be decreased.

In some implementations, the above-described methods include actuating a blood pump within the patient's vasculature, and determining cardiac output of the patient's heart using any of the foregoing systems and sensors. The blood pump's pumping speed may be adjusted based on the determined cardiac output. In some implementations, the hemodynamic support applied may be based on determining whether cardiac performance of the heart is increasing or decreasing over time.

In some implementations, a blood vessel sensor is provided. The blood vessel sensor may include a system for inducing blood flow within a patient's blood vessel. The system may be an intravascular system. The system may include a motor, and an impeller. In some implementations, the system for inducing blood flow within the patient's blood vessel comprises a cannula that is configured to extend within the left ventricle of a heart and a pressure sensor configured to detect at least one of: aortic pressure, left ventricular pressure, or differential pressure. The system for inducing blood flow within the patient's blood vessel may be intracardiac blood pump incorporating the impeller within a shroud. For example, the shroud may be a pump housing. The shroud may be sized for passage through the patient's blood vessel and may be coupled to the motor or other pump elements. The shroud may comprise one or more blood exhaust apertures or outlets.

The blood vessel sensor may also include a controller. The controller may be configured to detect changes in resistance of impeller rotation within the blood vessel. In some implementations, a constant impeller rotational speed is maintained based on the detected resistance of impeller rotation.

In some implementations, vascular compliance and vascular resistance may be calculated based on the change in resistance of impeller rotation using a transfer function. In some implementations, the transfer function is a Windkessel model. In some implementations, pump operation data may be transmitted to a computing device. The computing device may be located separately from the controller or onboard the controller. For example, the computing device may be a server stored remotely. In some implementations, the pump operation data includes at least one of pressure measurements, current measurements, change in resistance of impeller rotation, and flow estimations. In some implementations, the controller is further configured to receive pump operation commands from the computing device, wherein the pump operation commands are based on the pump operation data. For example, the computing device may calculate vascular resistance and compliance and alter pump operation accordingly.

In some implementations, the controller or the computing device is configured to determine a metric indicative of cardiac performance based on the vascular compliance and the vascular resistance. The metric indicative of cardiac performance may be at least one of: cardiac output, cardiac power output, stroke volume, stroke work, ejection fraction, cardiac contractility, ventricular elastance, cardiac index, a prediction of patient survival, or any suitable metric.

In some implementations, the controller is configured to adjust the impeller rotational speed based on at least one of: the vascular resistance, the vascular compliance, or the cardiac output. For example, the impeller rotational speed may be increased or decreased to provide more or less blood flow based on the patient's cardiac or vascular health.

In some implementations, the controller is configured to receive measurements indicative of aortic pressure for a time period, detect current delivered to the pump, and determine, based on the current delivered to the pump, rates of blood flow pumped by the system for the time period. The calculation of the vascular compliance and the vascular resistance may be based on the measurements indicative of aortic pressure and the rates of blood flow.

In some implementations, a controller is configured to perform any of the implementations, aspects, and methods described herein. For example, the controller may be the Automated Impella Controller (AIC) of Abiomed, Inc or any other suitable controller. In some implementations, the heart pump system includes a catheter; a motor; a rotor operatively coupled to the motor; a pump housing at least partially surrounding the rotor so that the actuating motor drives the rotor and pumps blood through the pump housing; one or more sensors, including a differential pressure sensor; and the controller. For example, the heart pump system may comprise the Impella 5.0 heart pump of Abiomed, Inc connected to an AIC or any other suitable system.

In some implementations, the controller comprises a display. Any of the foregoing calculations or features may be configured for display. For example, an aortic pressure waveform may be presented on a graphical user interface. Clinicians may view such displays and adjust operation of the pump based on their observations of hemodynamic parameters over time.

BRIEF DESCRIPTION OF THE DRAWINGS

FIG. 2 illustrates a process for determining the volume of blood pumped per heartbeat according to certain implementations;

FIG. 5 illustrates a process for determining total volume of blood pumped per heartbeat according to certain implementations;

DETAILED DESCRIPTION

Figure 1:
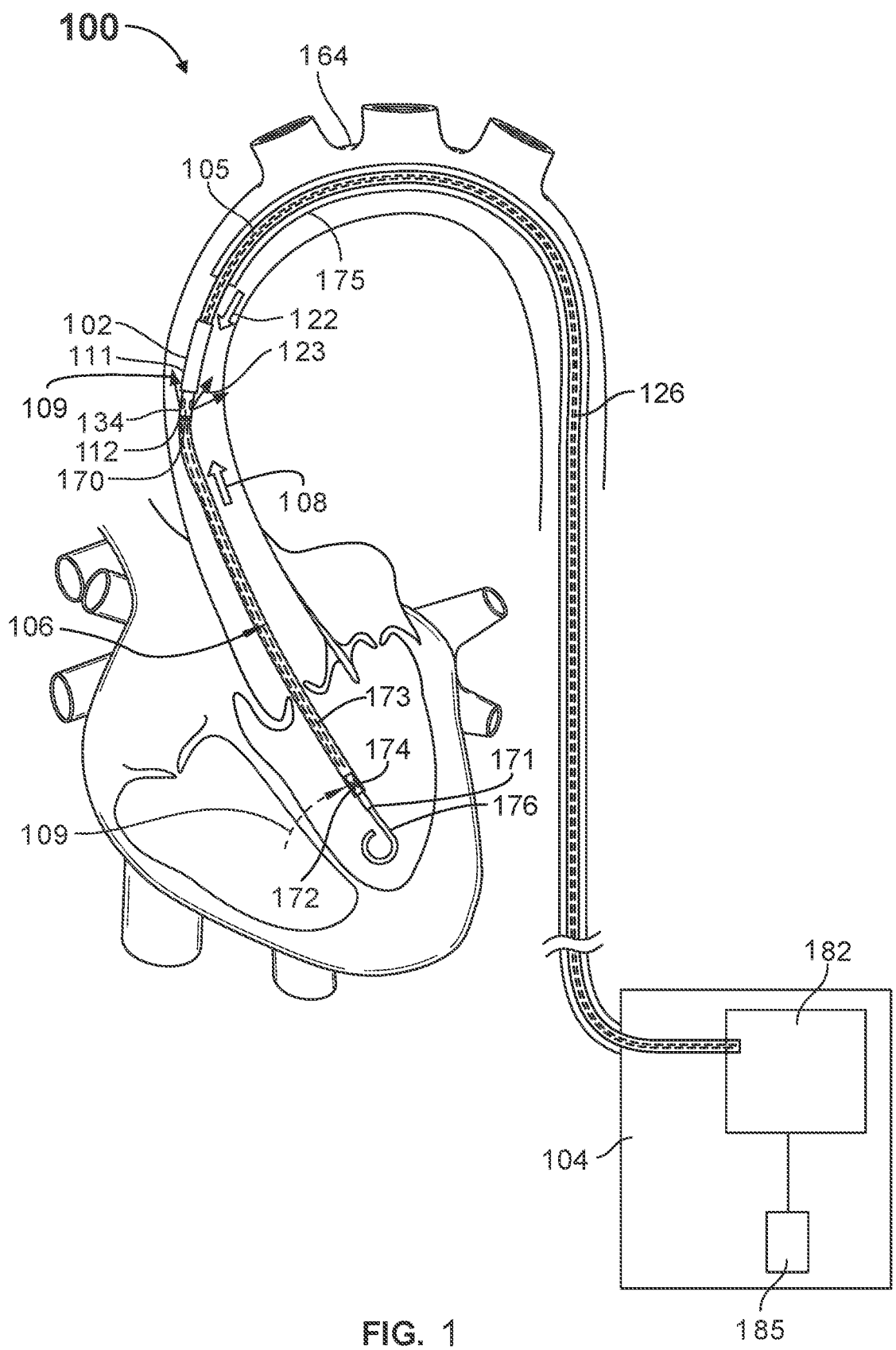
FIG. 1 show an illustrative heart pump system inserted into a blood vessel of a patient.

To provide an overall understanding of the systems and methods describe herein, certain illustrative embodiments will be described. Although the embodiments and features described herein are specifically described for use in connection with a percutaneous heart pump system, it will be understood that all the components and other features outlined below may be combined with one another in any suitable manner and may be adapted and applied to other types of cardiac therapy and heart pump systems, including heart pump systems implanted using a surgical incision, and the like.

The systems, devices, and methods described herein enable a support device residing completely or partially within an organ to assess that organ's function. In particular, the systems, devices and methods enable mechanical circulatory support systems, such as percutaneous ventricular assist devices, to be used to assess the function of the heart. For example, support devices such as blood pumps may be used in the treatment of cardiogenic shock, heart attack, or used to support a heart generally during coronary intervention.

Assessing the function of the heart using a mechanical circulatory support system can alert health professionals of changes in cardiac function and allow the degree of/level of support provided by the assist device (i.e., flow rate of blood pumped by the device) to be tailored to a particular patient's needs. For example, the degree of support can be increased when a patient's heart function is deteriorating, or the degree of support can be decreased when a patient's heart function is recovering and returning to a baseline of normal heart function. This can allow the device to dynamically respond to changes in heart function to promote heart recovery and can allow the patient to be gradually weaned off the therapy. Furthermore, assessment of the heart function can indicate when it is appropriate to terminate use of the heart pump system. Although some embodiments presented herein are directed to heart pump systems implanted across the aortic valve and residing partially in the left ventricle, the concepts can be applied to devices in other regions of the heart, the cardiovascular system, or the body.

Assessment of cardiac function may include leveraging heart-device interactions to determine heart parameters. The systems and methods described herein determine cardiac output based on aortic pressure measurements and flow output from a blood pump system. The flow may be a measurement or estimate determined from the motor current supplied to a motor at a given pump speed in an intravascular blood pump system. At least one advantage of the systems and methods described herein is that they allow the heart pump system to assess cardiac function without changing operation of the pump (e.g., pump speed), thereby minimizing risks associated with changing pump speeds. A decrease in pump speed involves a decrease in patient support, while an increase in pump speed may result in suction or other risks. Frequent and/or fast changes in pump speed may also lead to hemolysis or decrease of pump/motor performance. The use of an intravascular blood pump system to measure or estimate the necessary parameters to determine metrics indicative of cardiac performance also allows for continuous measurements of the heart's performance, because these metrics are acquired by the blood pump system already placed within the patient's vasculature.

Continuous measurement of vascular and cardiac performance by leveraging the effects of a heart pump system is a crucial step to provide additional clinical data to aid in titration of appropriate device support. However, more importantly, the systems and methods described herein demonstrate the impact and potential of device-arterial coupling to determine cardiac and vascular state. Unlike some invasive heart pump systems, which shunt blood out of the heart, the heart pump systems presented herein reside within the heart and work in parallel with native ventricular function. This allows the heart pump systems presented herein to be sensitive enough to detect native ventricular function unlike some more invasive devices. Thus, the systems, devices, and methods enable the use of heart pump systems not only as support devices, but also as diagnostic and prognostic tools. The heart pump systems can essentially function as active catheters that extract information about cardiac function by hydraulically coupling with the heart. In some implementations, the heart pump systems operate at a constant level (e.g., constant rotational speed of a rotor), while power delivered to the assist device is measured. In certain implementations, the speed of the rotor of the heart pump system may be varied (e.g., as a delta, step, or ramp function) to further probe the native heart function.

FIG. 1 show an illustrative heart pump system inserted into a blood vessel of a patient. Heart pump systems compatible with the present disclosure are disclosed in U.S. Patent Application Publication No. 2018-0078159-A1, the contents of which are hereby incorporated by reference in their entirety. Generally, any other heart pump system or system for obtaining physiological data from a patient may be used with the present disclosure. In some implementations, the systems and methods described herein may relate to the IMPELLA® family of devices (Abiomed, Inc., Danvers Mass.).

The heart pump system 100 may operate within a heart, partially within the heart, outside the heart, partially outside the heart, partially outside the vascular system, or in any other suitable location in a patient's vascular system. The heart pump system may be considered "in position" when cannula 173 is placed across the aortic valve such that a blood inlet (e.g., blood inlet 172) to the pump is within the left ventricle and an outlet (e.g., outlet openings 170) from the pump is within the aorta. The heart pump system 100 includes a heart pump 106 and a control system 104. All or part of the control system 104 may be in a controller unit separate/remote from the heart pump 106. In some implementations, the control system 104 is internal to the heart pump 106. The control system 104 and the heart pump 106 are not shown to scale. The pump system 100 includes an elongate catheter body 105, a motor housing 102 and a drive shaft in which a pump element is formed. The pump 100 includes a pump housing 134, and a motor housing 102 coupled to a cannula 173 at a distal end 111 of the motor housing 102. An impeller blade on the drive shaft may be rotated within a pump housing 134 to induce a flow of blood into the cannula 173 at a suction head 174. The suction head 174 provides a blood inlet 172 at the distal end portion 171 of the cannula 173. The flow 109 of blood passes through the cannula 173 in a first direction 108 and exits the cannula 173 at one or more outlet openings 170 of the cannula 173.

The rotation of the drive shaft within the pump housing 134 may also rotate a pump element within a bearing gap. A hemocompatible fluid may be delivered through the elongate catheter 105 through the motor housing 102 to a proximal end portion of the cannula 173 where the fluid is pressurized by the rotation of a pump element. The flow of hemocompatible fluid has a second direction 122 through the bearing gap of the pump. After exiting the bearing gap, the hemocompatible fluid may follow flow direction 123 and become entrained in the flow of blood and flows into the aorta with the blood.

The heart pump 100 is inserted into a vessel of the patient through a sheath 175. The pump housing 134 may enclose the rotor and internal bearings and may be sized for percutaneous insertion into a vessel of a patient. In some implementations, the pump may be advanced through the vasculature and over the aortic arch 164. Although the pump is shown in the left ventricle, the pump may alternatively be placed in the right heart, such that the blood is pumped from the patient's inferior vena cava or right atrium, through the right ventricle into the pulmonary artery.

A flexible projection 176 may also be included at a distal end portion 171 of the cannula 173, distal to the suction head 174, in order to position the heart pump 100 optimally in a vessel or chamber of the heart. The flexible projection 176 may prevent the suction head 174 from approaching the wall of the vessel where it may become stuck due to suction. The flexible projection 176 may extend the pump 100 mechanically, but not hydraulically, as the flexible projection 176 may be non-sucking. In some implementations, the flexible projection may be formed as a pigtail. In some aspects, the pump need not include a flexible projection.

The elongate catheter 105 houses a connection 126 that may comprise a fluid supply line and may also house electrical connection cables. The connection 126 may supply a hemocompatible fluid to the pump from a fluid reservoir that may be contained within control system 104.

The control system 104 includes controller 182 controls pump 106, including, for example, controlling power to the motor or controlling the motor speed. In some implementations, the control system 104 includes display screens to show measurements such as differential pressure signal and motor current. The control system 104 may include circuitry for monitoring the motor current for drops in current indicating air in the line, changes in differential pressure signal, flow position, suction, or any other suitable measurement. The control system 104 may include warning sounds, lights or indicators to alert an operator of sensor failures, disconnects or breaks in the connection 126, or sudden changes to patient health.

The motor 108 may operate at a speed required to maintain the rotor at a set speed. As a result and as further described below, the motor current drawn by the motor to maintain the rotor speed can be monitored and used to understand the underlying cardiac state. For example, motor current may be used to determine flow through the heart.

The heart pump may operate at a variety of pump speeds or P-levels. P-level is the performance level of the heart pump system and related to flow control of the system. As P-level increases, the flow rate, motor current, and revolutions per minute associated with the heart pump system increase; thus, higher P-levels correspond to higher flow rates and revolutions per minute associated with the heart pump system. For example, power level P-1 may corresponds to a first number of rotations per minute (RPM) for the rotor, while power level P-2 corresponds to a second number of RPM. In some examples, the pump operates at ten different power levels ranging from P-0 through P-9. These P-levels may correspond to 0 RPM through 100,000 RPM or any suitable number. Changing the speed of the rotor changes the CO of the heart.

The control system 104 can include a current sensor (not shown). The controller 182 supplies current to the motor 108 by the connection 126 such as through one or more electrical wires. The current supplied to the motor 108 via the connection 126 is measured by the current sensor. The load that the motor of a mechanical pump experiences is pressure head, or the difference between the aortic and left ventricular pressure. The heart pump 106 experiences a nominal load during steady state operation for a given pressure head, and variations from this nominal load are a result of changing external load conditions, for example the dynamics of left ventricular contraction. Changes to the dynamic load conditions alter the motor current required to operate the pump rotor at a constant, or substantially constant, speed. As described above, the motor may operate at a speed required to maintain the rotor at a set speed, and the motor current drawn by the motor to maintain the rotor speed can be monitored and used to understand the underlying cardiac state. The cardiac state can be even more precisely quantified and understood by simultaneously monitoring the pressure head during the heartbeat cycle using a pressure sensor 112. The heart parameter estimator 185 receives current signals from the current sensor as well as pressure signals from the pressure sensor 112. The heart parameter estimator 185 uses these current and pressure signals to characterize the heart's function. The heart parameter estimator 185 may access stored look-up tables to obtain additional information to characterize the heart's function based on the pressure and current signals. For example, the heart parameter estimator 185 may receive an aortic pressure from the pressure sensor 112, and using look-up tables, may use the motor current and pump speed to determine a delta pressure between the aorta and the ventricle.

In some implementations, pressure sensor 112 is an aortic pressure sensor. In some implementations, pressure sensor 112 is a flexible membrane integrated into the cannula 172 configured to measure differential pressure. One side of the sensor is exposed to the blood pressure on the outside of the cannula and the other side is exposed to the pressure of the blood inside of the cannula. The sensor generates an electrical signal (the differential pressure signal) proportional to the difference between the pressure outside the cannula and the pressure inside, which may be displayed by the heart pump system. When the heart pump system is placed in the correct position across the aortic valve, the top (outer surface) of the sensor is exposed to the aortic pressure and the bottom (inner surface) of the sensor is exposed to the ventricular pressure. Therefore, the differential pressure signal is approximately equal to the difference between the aortic pressure and the ventricular pressure. In some implementations, the system includes both differential and aortic pressure sensors.

FIG. 2 illustrates a process 200 for determining cardiac output. The process 200 can be performed using the heart pump system 100 of FIG. 1 or any other suitable pump. In some implementations the pump is an intravascular blood pump device placed within the patient's heart via percutaneous insertion. The pump may be introduced to the patient because the patient is in cardiogenic shock or otherwise experiencing a decline in health. The pump may be positioned across the aortic valve such that a blood inlet (e.g., blood inlet 172 of FIG. 1) to the pump is within the left ventricle and an outlet (e.g., outlet openings 170 of FIG. 1) from the pump is within the aorta. The pump contributes with native heart operation such that CO from the heart is equal to native CO plus pump output.

In step 202, hemodynamic support is applied to a heart at a first pumping rate. In some implementations, the pumping rate may correspond to a speed of rotation of a rotor. For example, the pump speed may be 10,000 RPM, 20,000 RPM, 30,000 RPM, 40,000 RPM, 50,000 RPM, 60,000 RPM, 70,000 RPM, 80,000 RPM, 90,000 RPM, 100,000 RPM, or any suitable speed. A pump speed may correspond to a power level, or P-level, as described below in relation to FIG. 1. For example, the pump speed may be P-1, P-2, P-3, P-4, P-5, P-6, P-7, P-8, or P-9. In some implementations, the pumping rate may instead correspond to the rate at which a chamber of the pump fills up with and releases blood. The pumping rate is supplied over a plurality of heartbeats of the heart. Each heartbeat includes a systolic rise, a dicrotic notch, and a diastolic fall that occurs after the dicrotic notch.

In step 204, at least three aortic pressure measurements are detected during the diastolic fall of a specific beat of the plurality of beats. In some implementations, aortic pressure is continuously measured or is periodically sampled, and a plurality of aortic pressure measurements are detected. For example, pressure may be sampled at a rate of 1, 2, 3, 10, 20, 30, 100, 200, 300, 1000, 2000, 3000, or any other suitable number of samples per second. In some examples, aortic pressure is only sampled during the diastolic fall. In some examples, aortic pressure is constantly or periodically measured.

Figure 3:
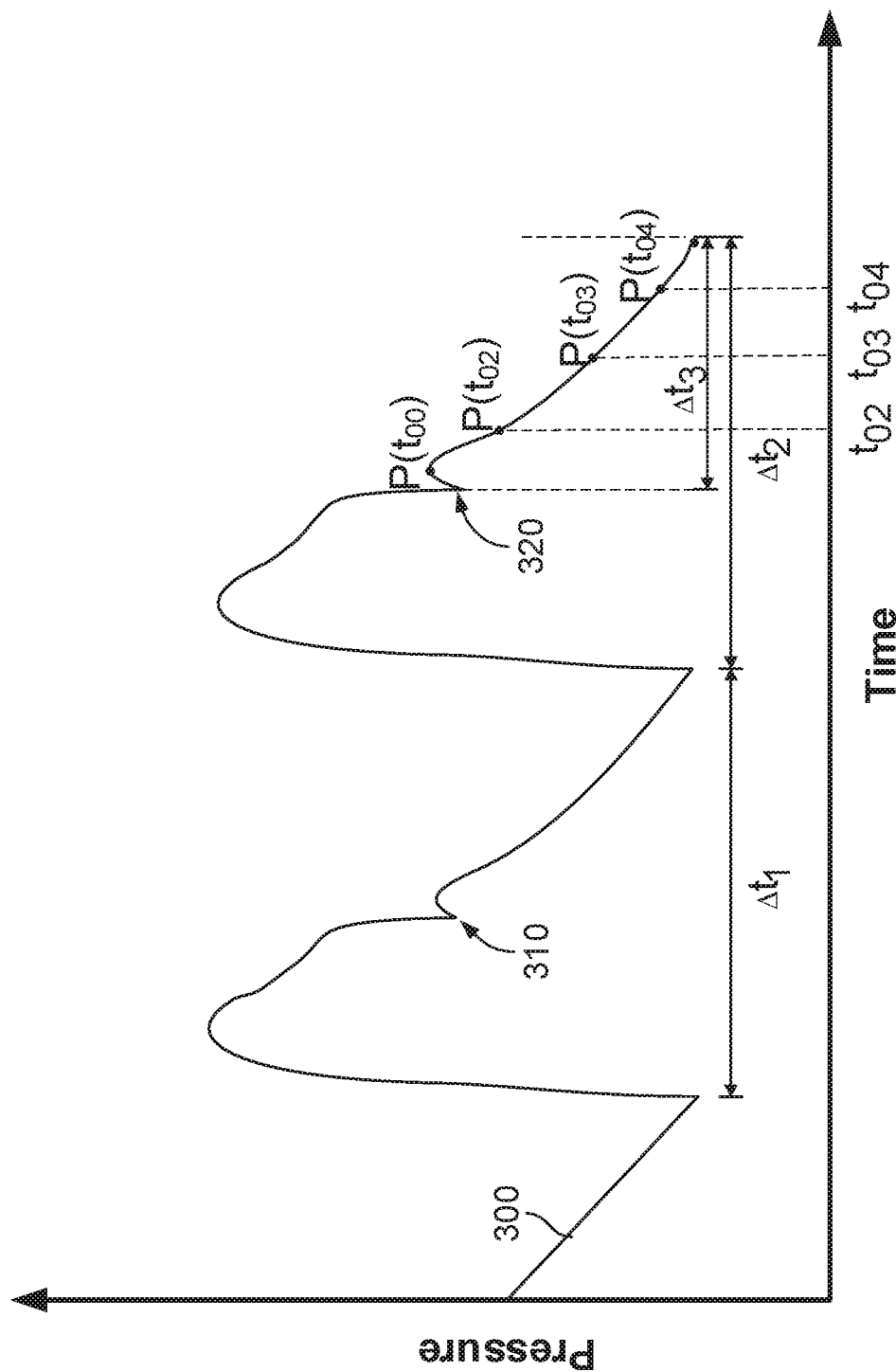
FIG. 3 shows a plot of pressure versus time for a heart pump system according to certain implementations.

In step 206, at least three blood flow pumped by the intravascular blood pump are determined. As shown in FIG. 3 and described above, pressure may be measured at a series of points during a diastolic time period. For each of these pressure measurements, pressure is measured and flow may be estimated based on current supplied to the pump to maintain a rotor speed. This mathematical relationship between pump speed and motor current to a flow estimate may be implemented by setting up a look-up table where the pump speed and motor current are the indices to the table and the flow values in the table is pre-populated through bench testing. Another way is to pre-determine flow for a sub-set of possible combinations of pump speed and motor current. For example, if the flow at a pump speed of 40,000 RPM and a motor current of 500 mA and the flow at a pump speed of 40,000 RPM and a motor current of 510 mA are known as $i_1$ and $i_2$, respectively, then the flow at a pump speed of 40,000 RPM and a motor current of 505 mA can be calculated by taking the average of $i_1$ and $i_2$. The pressure and flow measurements, in combination with the known time of measurement, are compared between two times to calculate heart parameters such as systemic vascular resistance and compliance.

In step 208, cardiac output during the specific beat is determined based on the aortic pressure and blood flow measurements. A Windkessel model with two current sources, $i_h$ and $i_p$ in parallel with each other and with a resistance R and compliance C, may be used to simulate the aortic pressure. The governing equation for this model is:

$$C\frac{dP}{dt} + \frac{P}{R} = i_h + i_p \quad (1)$$

where C is compliance, P is pressure, R is vascular resistance, $i_h$ is flow from native heart operation and $i_p$ is flow from the pump. During diastole, however, the aortic valve is closed, so the only flow through the left ventricle is from the pump positioned across the valve. By discounting the heart current source and assuming pump flow is constant, the model can thus be simplified as follows:

$$P = P_0 e^{-\frac{t}{RC}} + i_p R \quad (2)$$

where $P_0$ is the initial aortic pressure during diastole. In some implementations, flow from the pump $i_p$ is estimated from current flow to the motor of the heart pump system to maintain constant speed. Pressure P may be measured at a variety of points within a single diastolic period to characterize and deconstruct the pressure waveform, as shown in FIG. 3 and described below. For example, pressure may be known at three times. Flow $i_p$ may be estimated at the same three times as well. Setting up three pressure equations, one each for the three times respectively, based on Equation (2), R and C values may be calculated. For example, once R and C have been determined using the Windkessel model described above, CO for the heart may be determined by plugging the calculated R and C values into Equation (1) above and solving for in to determine volumetric flow contributed by native heart function.

Operation of the pump may be adjusted, based on the calculated CO value. Adjusting pump operation may include increasing pump speed, decreasing pump speed, adjusting pump placement, turning the pump off, or any other suitable adjustment. For example, if the CO is below a threshold, the pump speed may be increased, while if CO is above a threshold, the pump speed may be decreased.

FIG. 3 shows a plot 300 of pressure versus time for a heart pump system, according to certain implementations. The y-axis of plot 300 represents aortic pressure in mmHg, while the x-axis represents time as a percentage of a heartbeat length. In particular, plot 300 shows that pressure may be measured at a series of points $P_0$-$P_5$ during diastole of a heartbeat. $\Delta t_1$ represents a time of a first heartbeat and $\Delta t_2$ represents a time of a second heartbeat after the first heartbeat. Time periods $\Delta t_1$ and $\Delta t_2$ occur while the heart pump system is placed at least partially within the patient's heart. Point 310 represents the dicrotic notch during the first heartbeat and point 320 represents the dicrotic notch during the second heartbeat. Diastolic time period $\Delta t_3$ represent the diastolic period of the second heartbeat. During time periods $\Delta t_1$, $\Delta t_2$, and $\Delta t_3$, the pump operates at a first pump speed. In some implementations, the pump operates at a second pump speed during time period $\Delta t_3$. For example, pump speed may be increased during time period $\Delta t_3$. At higher pump speeds, the measured aortic pressure and total flow are higher compared to lower pump speeds.

At a given known point in time $t_{02}$ within diastolic period $\Delta t_3$, pressure $P(t_{02})$ is known; at a second known point in time $t_{03}$ within diastolic period $\Delta t_3$, pressure $P(t_{03})$ is known; and at a third known point in time $t_{04}$ within diastolic period $\Delta t_3$, pressure $P(t_{04})$ is known. At each of these times within the diastolic period $\Delta t_3$, the pump flow is known from motor current supplied to the pump motor at that point in time. Thus, the following equations may be used to calculate $P_0$, R and C:

$$P(t_{02}) = P_0 e^{-\frac{t_{02}}{RC}} + i_p(t_{02}) * R \quad (3)$$

$$P(t_{03}) = P_0 e^{-\frac{t_{03}}{RC}} + i_p(t_{03}) * R \quad (4)$$

$$P(t_{04}) = P_0 e^{-\frac{t_{04}}{RC}} + i_p(t_{04}) * R \quad (5)$$

These steps may be repeated for each time point within diastolic period $t_3$. R and C values calculated for each set of times (e.g., $t_{02}$ and $t_{04}$, $t_{02}$ and $t_{03}$, etc.) may differ slightly. The measured R and C values may be averaged to arrive at representative systemic vascular resistance and compliance values for the heart. In some implementations, R and C values may be periodically calculated to determine how the values change over time as a patient is treated. In some implementations, cardiac output may be determined using the calculated R and C values. For example, determining cardiac output may include determining cardiac output of a plurality of specific beats within the plurality of beats and applying at least one of a summation, average, or linear regression on the determined cardiac outputs to determine a cumulative indicator of cardiac output of the heart.

Figure 4:
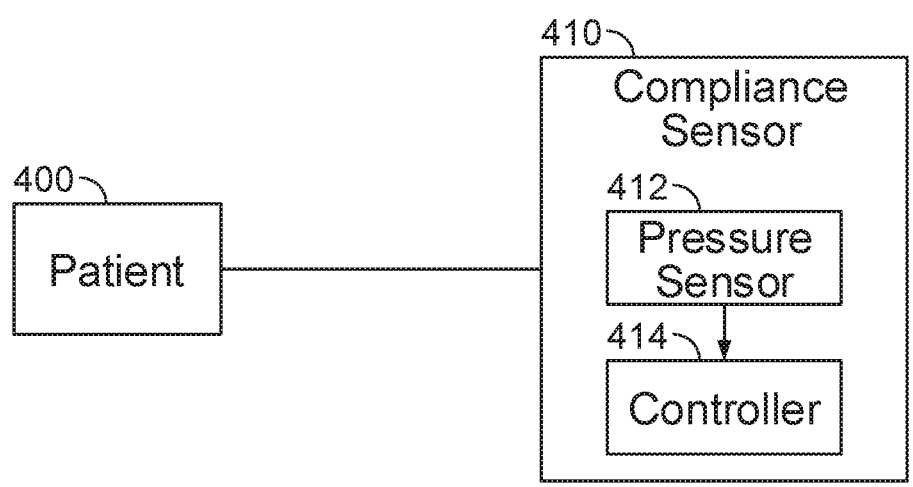
FIG. 4 shows a CO sensor coupled to a patient according to certain implementations.

FIG. 4 shows a compliance sensor 410 coupled to a patient 400. Compliance sensor 410 may comprise a variety of hardware elements configured to perform the methods described herein, as well as additional processes. In some implementations, the compliance sensor includes an intravascular blood pump (e.g., pump 202 of FIG. 1). The intravascular blood pump may be configured to be placed at least partially within a patient's heart. In some implementations, the intravascular blood pump includes a cannula, an impeller configured to be rotated within a blood vessel and pump blood through the cannula, and a drive mechanism configured to impart power to turn the impeller. In some implementations, the cannula may be configured to extend across an aortic valve such that a distal end of the cannula is within a left ventricle and a proximal end of the cannula is within the aorta. For example, the heart pump system may be considered "in position" when the cannula is placed across the aortic valve such that a blood inlet to the pump is within the left ventricle and an outlet from the pump is within the aorta. The drive mechanism may include an onboard motor, a drive cable, a drive shaft, or any other suitable element or combination thereof.

In some implementations, compliance sensor 410 includes an elongate catheter body coupled to a cannula. The elongate catheter may include a drive cable, electrical wiring connecting the blood pump to a control system, any suitable element, or any combination thereof. In some implementations, the blood pump includes a pump housing and a motor housing coupled to the cannula at a distal end of the motor housing. The impeller may be rotated within the pump housing to induce a flow of blood into the cannula.

Compliance sensor 410 includes a pressure sensor configured to detect pressure within the blood vessel arising at least in part from the pumping of blood within the vessel. For example, the pressure sensor may be a differential pressure sensor that is part of a blood pump. One side or surface of the differential pressure sensor may be exposed to the aortic pressure, a second side or surface of the differential pressure sensor may be exposed to the ventricular pressure, and the differential pressure sensor may measure the difference between the aortic and ventricular pressures. As another example, pressure sensor 412 may comprise a pressure measurement lumen configured to measure aortic pressure.

Compliance sensor 410 includes controller 414. Controller 414 is coupled to pressure sensor 412. Controller 414 may coupled directly or indirectly to pressure sensor 412. For example, control 414 may be connected to pressure sensor 412 via electrical wiring, a wireless signal, or any other suitable means. Controller 414 is configured to detect signals from the pressure sensor indicative of blood pressure. All or part of controller 414 may be in a controller unit separate/remote from an intravascular blood pump. In some implementations, the control system is internal to an intravascular blood pump.

In some implementations, controller 414 is configured to detect changes in resistance of impeller rotation within the blood vessel. For example, resistance may be calculated at a variety of points in time based on pressure and flow measurements of the heart, as described above in relation to FIG. 1.

In some implementations, controller 414 is configured to maintain a constant impeller rotational speed, based on the detected resistance of impeller rotation. Current supplied to the impeller motor may change based on the necessary current needed to maintain motor speed. Thus, motor current may be correlated to flow through the heart.

In some implementations, controller 414 is configured to calculate, based on the change in resistance of impeller rotation, vascular compliance and vascular resistance using a transfer function. For example, the vascular compliance and resistance may be determined as described above in relation to FIG. 3. In another example, while the pump speed is maintained at a constant speed (speed$_1$), a set of diastolic aortic pressure measurements $P_1(t)$ and a set of pump flow $i_1(t)$ measurements are determined for a set of times (e.g., t equals $t1_{01}$, $t1_{02}$, $t1_{03}$, etc.). Then the controller may set the pump to a different constant speed (speed2) and obtain a second set of diastolic aortic pressure measurements $P_2(t)$ and a second set of pump flow measurements $i_2(t)$ for a second set of times (e.g., t equals $t2_{01}$, $t2_{02}$, $t2_{03}$, etc.). The difference in the two sets of pressure measurements $P_1(t)$ and $P_2(t)$ and the difference in the two sets of pump flow $i_1(t)$ and $i_2(t)$ can be used to calculate the vascular resistance via the following equation:

$$R = \frac{\text{mean}(P_1(t)) - \text{mean}(P_2(t))}{\text{mean}(i_1(t)) - \text{mean}(i_2(t))} \quad (6)$$

FIG. 5 illustrates a process 500 for determining total volume of blood pumped per heartbeat. The process 500 can be performed using the heart pump system 100 of FIG. 1 or any other suitable pump. In some implementations, the pump is an intravascular blood pump device placed within the patient's heart via percutaneous insertion. In some implementations, the pump may be a surgically implanted device, a left ventricular assist device, a counterpulsation device, an expandable heart pump, or any other suitable device. The pump may be introduced to the patient because the patient is in cardiogenic shock or otherwise experiencing a decline in health. The pump may be positioned across the aortic valve such that a blood inlet (e.g., blood inlet 172 of FIG. 1) to the pump is within the left ventricle and an outlet (e.g., outlet openings 170 of FIG. 1) from the pump is within the aorta. The pump contributes with native heart operation such that CO from the heart is equal to native CO plus pump output.

At step 502, a hemodynamic parameter is monitored during operation of a heart pump at a first pump speed. A hemodynamic parameter may be any parameter relating to the flow of blood within the organs and tissues of the body. For example, the hemodynamic parameter may include at least one of heart rate, blood pressure, arterial oxygen saturation, mixed venous saturation, central venous oxygen saturation, arterial blood pressure, mean arterial pressure, right arterial pressure, central venous pressure, right ventricular pressure, pulmonary artery pressure, mean pulmonary artery pressure, pulmonary artery occlusion pressure, left atrial pressure, aortic pressure, differential pressure, left ventricular end pressure, stroke volume, stroke volume index, stroke volume variation, systemic vascular resistance, systemic vascular resistance index, pulmonary vascular resistance, pulmonary vascular resistance index, pulmonary vascular resistance, pulmonary vascular resistance index, left ventricular stroke work, left ventricular stoke work index, right ventricular stroke work, right ventricular stroke work index, coronary artery perfusion pressure, right ventricular end diastolic volume, right ventricular end diastolic volume index, right ventricular end systolic volume, right ventricular ejection fraction, arterial oxygen content, venous oxygen content, arterial-venous oxygen content difference, oxygen delivery, oxygen delivery index, oxygen consumption, oxygen consumption index, oxygen extraction ration, oxygen extraction index, total peripheral resistance, CO, cardiac index, and CPO. A pump speed is the speed of operation of the pump and corresponds to the amount of blood flow provided by the pump's operation. In some implementations, the pump speed may correspond to a speed of rotation of a rotor. For example, the pump speed may be 10,000 RPM, 20,000 RPM, 30,000 RPM, 40,000 RPM, 50,000 RPM, 60,000 RPM, 70,000 RPM, 80,000 RPM, 90,000 RPM, 100,000 RPM, or any suitable speed. A pump speed may correspond to a power level, or P-level, as described above in relation to FIG. 1. For example, the pump speed may be P-1, P-2, P-3, P-4, P-5, P-6, P-7, P-8, P-9, or any other suitable value. In some implementations, the pump speed may instead correspond to the rate at which a chamber of the pump fills up with and releases blood.

At step 504, a diastolic period of a heartbeat cycle is identified, based on a shape of the hemodynamic parameter over time. The diastolic period is the time for a heart to complete diastole—the phase of the heartbeat when the heart muscle relaxes and allows the chambers to fill with blood. For example, the diastolic period may be 0.05 seconds, 0.1 seconds, 0.2 seconds, 0.3 seconds, 0.4 seconds, 0.5 seconds, 0.6 seconds, 0.7 seconds, 0.8 seconds, 0.9 seconds, 1 second or any suitable length of time.

At step 506, a time-variant relationship between aortic pressure and blood flow during the diastolic period is determined. The time-variant relationship may be a Windkessel model with two current sources, $i_h$ and $i_p$ in parallel with each other and with a resistance R and compliance C. The governing equation for this model is:

$$C\frac{dP}{dt} + \frac{P}{R} = i_h + i_p \quad (1)$$

where C is compliance, P is pressure, R is systemic vascular resistance, $i_h$ is flow from native heart operation and $i_p$ is flow from the pump. During diastole, however, the aortic valve is closed, so the only flow through the left ventricle is from the pump positioned across the valve. By discounting the heart current source and assuming pump flow is constant, the model can thus be simplified as follows:

$$P = P_0 e^{-\frac{t}{RC}} + i_p R \qquad (2)$$

where $P_0$ is the initial aortic pressure during diastole. In some implementations, flow from the pump $i_p$ is estimated from current flow to the motor of the heart pump system to maintain constant speed. Pressure P may be measured at a variety of points within a single diastolic period to characterize and deconstruct the pressure waveform, as describe below in relation to FIG. 3. In some implementations, the heart pump is operated at a constant speed. In some implementations described herein, the speed of the pump may be altered to "ping" the heart.

At step 508, a total volume of blood pumped per heartbeat, which is representative of cardiac performance, calculated based on the time-variant relationship between aortic pressure and blood flow during the diastolic period. For example, once R and C have been determined, CO for the heart may be determined (e.g., as described below in relation to FIG. 7). In some implementations, other metrics indicative of cardiac performance may be computed. For example, the metric indicative of cardiac performance may be ventricular resistance, ventricular compliance, CO, CPO, stroke volume, stroke work, ejection fraction, cardiac index, or a prediction of patient survival. Many metrics indicative of cardiac performance are interrelated. For example, CO is determined based on the flow rate of the blood through and past the pump. The stroke volume is an index of left ventricular function which formula SV=CO/BR, where SV is the stroke volume, CO is the cardiac output, and HR is the heart rate. Stroke work is the work done by the ventricle to eject a volume of blood and can be calculated from the stroke volume according to the equation SW=SV*MAP, where SW is the stroke work, SV is the stroke volume, and MAP is the mean arterial pressure. Cardiac work is calculated by the product of stroke work and heart rate. CPO is a measure of the heart function representing cardiac pumping ability in Watts. CPO is calculated using the equation CPO=mAoP*CO/451, where CPO is the cardiac power output, mAoP is the mean aortic pressure, CO is the cardiac output, and 451 is a constant used to convert mmHg×L/min into Watts. The ejection fraction can be calculated by dividing the stroke volume by the volume of blood in the ventricle. Other parameters, such as chamber pressure, preload state, afterload state, heart recovery, flow load state, variable volume load state, and/or heartbeat cycle flow state can be calculated from these values or determined via these parameters.

In some implementations, operation of the pump is adjusted, based on the metric indicative of cardiac performance. Adjusting pump operation may include increasing pump speed, decreasing pump speed, adjusting pump placement, turning the pump off, or any other suitable adjustment. For example, if total volume of blood pumped is below a threshold, the pump speed may be increased, while if the blood volume is above a threshold, the pump speed may be decreased.

In some implementations, the above-described methods include actuating a blood pump within the patient's vasculature, and determining cardiac output of the patient's heart using any of the foregoing systems and sensors. The blood pump's pumping speed may be adjusted based on the determined cardiac output.

Figure 6:
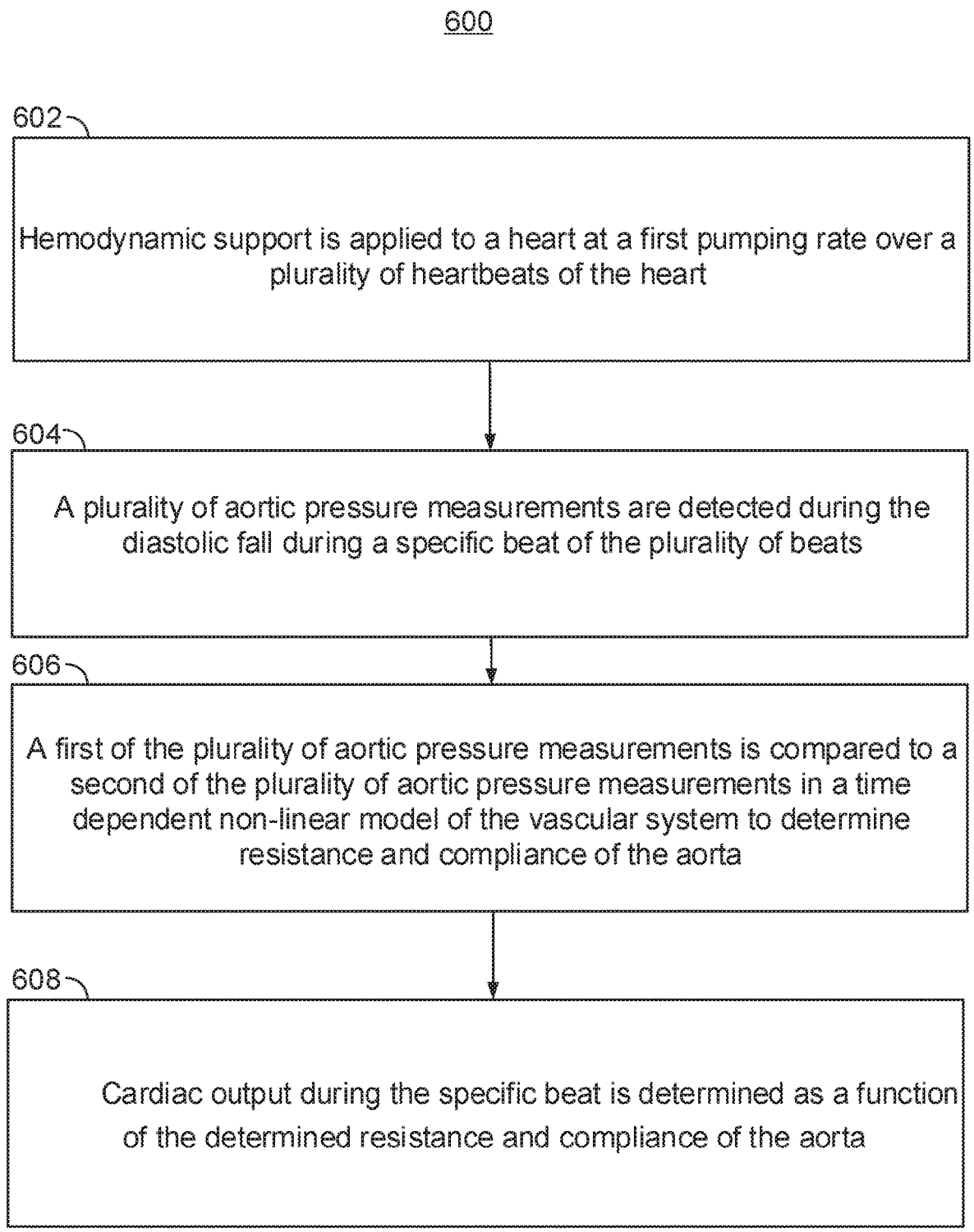
FIG. 6 illustrates a process for determining cardiac output according to certain implementations.

FIG. 6 illustrates a process 600 for determining cardiac output. The process 600 can be performed using the heart pump system 100 of FIG. 1 or any other suitable pump. In some implementations, the pump is an intravascular blood pump device placed within the patient's heart via percutaneous insertion. The pump may be introduced to the patient because the patient is in cardiogenic shock or otherwise experiencing a decline in health. The pump may be positioned across the aortic valve such that a blood inlet (e.g., blood inlet 172 of FIG. 1) to the pump is within the left ventricle and an outlet (e.g., outlet openings 170 of FIG. 1) from the pump is within the aorta. The pump contributes with native heart operation such that CO from the heart is equal to native CO plus pump output.

In step 602, hemodynamic support is applied to a heart at a first pumping rate. The hemodynamic pumping rate is supplied over a plurality of heartbeats of the heart. Each heartbeat includes a systolic rise, a dicrotic notch, and a diastolic fall that occurs after the dicrotic notch. For example, the hemodynamic pumping rate may be provided over two, three, four, ten, twenty, thirty, one hundred, two hundred, or any other suitable number of heartbeats.

In step 604, a plurality of aortic pressure measurements are detected during the diastolic fall during a specific beat of the plurality of beats. For example, pressure may be sampled at a rate of 1, 2, 3, 10, 20, 30, 100, 200, 300, 1000, 2000, 3000, or any other suitable number of samples per second. In some examples, aortic pressure is only sampled during the diastolic fall. In some examples, aortic pressure is constantly or periodically measured. In some examples, the sampling rate of aortic pressure is altered during the diastolic fall.

In step 606, a first of the plurality of aortic pressure measurements is compared to a second of the plurality of aortic pressure measurements in a time dependent non-linear model of the vascular system to determine systemic vascular resistance and compliance. In some implementations, at least one aortic pressure measurement is taken at the end of diastole, when the cardiac output occurs solely by the operation of a blood pump. For example, as shown in FIG. 3 and described above, pressure may be measured at a series of points during a diastolic time period. For each of these pressure measurements, pressure may be measured and flow may be estimated. The pressure and flow measurements, in combination with the known time of measurement, may be compared between two times to calculate heart parameters such as aortic resistance and compliance.

In step 608, cardiac output during the specific beat is determined as a function of the determined systemic vascular resistance and compliance. In some implementations, determining cardiac output includes determining cardiac output of a plurality of specific beats within the plurality of beats and applying at least one of a summation, average, or linear regression on the determined cardiac outputs to determine a cumulative indicator of cardiac output of the heart. The cumulative indicator of cardiac output of the heart may be indicative of cardiac performance or overall patient health.

Figure 7:
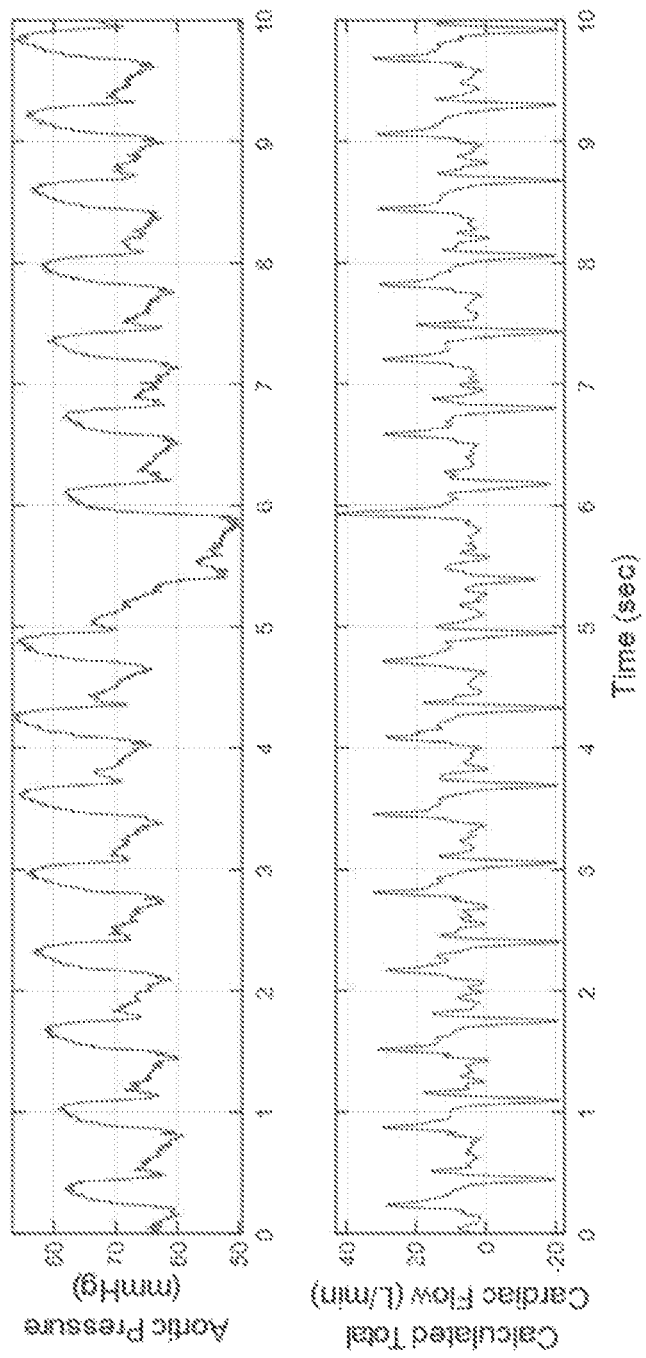
FIG. 7 shows plots of pressure versus time and flow versus time for a heart pump system according to certain implementations.

FIG. 7 shows two plots, one of aortic pressure and one of cardiac flow for the same ten-second period. The y-axis of the upper plot represents aortic pressure in mmHg, while the x-axis represents time in seconds. The y-axis of the lower plot represents calculated total cardiac flow in liters per minute, while the x-axis represents time in seconds. In this example, systemic vascular resistance R and compliance C are known. For example, R and C may be calculated using aortic pressure measurements taken during the depicted ten second time period in combination with pump data as described above. The total cardiac flow $i_h+i_p$ is calculated using R, C, and the aortic pressure waveform by applying Equation (1):

$$C\frac{dP}{dt} + \frac{P}{R} = i_h + i_p \quad (1)$$

CO can be calculated by taking the average of the total cardiac flow $i_h+i_p$ resulting from Equation (1) over a period of time (e.g., 5 seconds, 10 seconds, or 30 seconds). In the example in FIG. 7, the period of time is 10 seconds. The average R value for the time period is 0.6143 mmHg*sec/ml and the average C value is 1.5 mL/mmHg, resulting in a calculated CO of 6.9 L/min.

The foregoing is merely illustrative of the principles of the disclosure, and the apparatuses can be practiced by other than the described aspects, which are presented for purposes of illustration and not of limitation. It is to be understood that the apparatuses disclosed herein, while shown for use in percutaneous insertion of heart pumps, may be applied to apparatuses in other applications requiring hemostasis.

Variations and modifications will occur to those of skill in the art after reviewing this disclosure. The disclosed features may be implemented, in any combination and subcombination (including multiple dependent combinations and sub-combinations), with one or more other features described herein. The various features described or illustrated above, including any components thereof, may be combined or integrated in other systems. Moreover, certain features may be omitted or not implemented.

The systems and methods described may be implemented locally on a heart pump system or a controller of a heart pump system, such as the AIC. The heart pump system may comprise a data processing apparatus. The systems and methods described herein may be implemented remotely on a separate data processing apparatus. The separate data processing apparatus may be connected directly or indirectly to the heart pump system through cloud applications. The heart pump system may communicate with the separate data processing apparatus in real-time (or near real-time).

In general, aspects of the subject matter and the functional operations described in this specification can be implemented in digital electronic circuitry, or in computer software, firmware, or hardware, including the structures disclosed in this specification and their structural equivalents, or in combinations of one or more of them. Aspects of the subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program may correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices.

Examples of changes, substitutions, and alterations are ascertainable by one skilled in the art and could be made without departing from the scope of the information disclosed herein. All references cited herein are incorporated by reference in their entirety and made part of this application.

We claim:

1. A method comprising:
    applying hemodynamic support to a heart via a blood pump, the hemodynamic support comprising pumping blood at a first pumping rate during a plurality of beats of the heart;
    detecting a first aortic pressure measurement at a first time and a second aortic pressure measurement at a second time, wherein the first time and the second time occur at different times during a diastolic fall of a specific beat within the plurality of beats, and wherein the diastolic fall occurs after a dicrotic notch of the specific beat;
    determining a first rate of blood flow pumped by the blood pump at the first time and a second rate of blood flow pumped by the blood pump at the second time; and determining a cardiac output of the specific beat based on the first aortic pressure measurement, the second aortic pressure measurement, the first rate of blood flow, and the second rate of blood flow; and adjusting the hemodynamic support applied to the heart based on the determined cardiac output.

2. The method of claim 1, wherein determining the cardiac output of the specific beat comprises:

obtaining, using the first aortic pressure measurement, the second aortic pressure measurement, the first rate of blood flow, and the second rate of blood flow, a time dependent non-linear model of a vascular system to determine systemic vascular resistance and compliance; and determining the cardiac output of the specific beat based on the determined systemic vascular resistance and compliance.

3. The method of claim 2, wherein the time dependent non-linear model is a Windkessel model.

4. The method of claim 2, further comprising:

determining a first plurality of cardiac output values, wherein each cardiac output value of the first plurality of cardiac output values corresponds to a respective beat of a first set of beats within the plurality of beats; and determining a first cumulative indicator of cardiac output of the heart based on the first plurality of cardiac output values.

5. The method of claim 4, further comprising:

comparing a first cardiac output value to a second cardiac output value, wherein the first plurality of cardiac output values comprises the first and second cardiac output values;

determining, based on the comparison between the first cardiac output value and the second cardiac output value, a change in cardiac performance of the heart; and altering the hemodynamic support based on the determined change in cardiac performance of the heart.

6. The method of claim 4, wherein determining the first cumulative indicator of cardiac output of the heart comprises applying at least one of a summation, average, or linear regression on the first plurality of cardiac output values to calculate the first cumulative indicator of cardiac output of the heart.

7. The method of claim 6, further comprising:

determining a second cumulative indicator of cardiac output of the heart for a second set of beats within the plurality of beats, wherein the second set of beats occurs after the first set of beats;

comparing the first cumulative indicator of cardiac output to the second cumulative indicator of cardiac output;

determining, based on the comparison between the first cumulative indicator and the second cumulative indicator, (i) an increase in cardiac performance of the heart or (ii) a decrease in cardiac performance of the heart; and altering the hemodynamic support based on the determined increase or decrease of cardiac performance of the heart.

8. The method of claim 7, wherein determining the second cumulative indicator comprises:

determining a second plurality of cardiac output values, wherein each cardiac output value of the second plurality of cardiac output values corresponds to a respective beat of the second set of beats; and applying at least one of a summation, average, or linear regression on the second plurality of cardiac output values to calculate the second cumulative indicator of cardiac output of the heart.

9. The method of claim 2, wherein the systemic vascular resistance and compliance are indicative of resistance and compliance of an aorta.

10. The method of claim 9, wherein determining the cardiac output of the specific beat further comprises taking an average of total cardiac flow over a period of time.

11. The method of claim 10, wherein the period of time is the length of the specific beat.

12. The method of claim 1, wherein determining the cardiac output of the specific beat comprises:

detecting a plurality of aortic pressure measurements at a plurality of different times during the diastolic fall of the specific beat, wherein each aortic pressure measurement of the plurality of aortic pressure measurements corresponds to a time of the plurality of different times, and wherein the plurality of aortic pressure measurements includes the first aortic pressure measurement and the second aortic pressure measurement;

determining a plurality of rates of blood flow pumped by the blood pump at the plurality of different times, wherein the plurality of rates of blood flow includes the first rate of blood flow and the second rate of blood flow;

obtaining, using the plurality of aortic pressure measurements and the plurality of rates of blood flow, a plurality of time dependent non-linear models of a vascular system to determine a plurality of systemic vascular resistance and compliance values;

determining a plurality of cardiac output values based on the determined plurality of systemic vascular resistance and compliance values; and applying at least one of a summation, average, or linear regression to the determined plurality of cardiac output values to calculate the cardiac output of the specific beat.

13. The method of claim 12, further comprising:

determining a cardiac output of a second beat within the plurality of beats, wherein the second beat occurs after the specific beat;

comparing the cardiac output of the specific beat to the cardiac output of the second beat;

determining, based on the comparison between the cardiac output of the specific beat and the cardiac output of the second beat, (i) an increase in cardiac performance of the heart or (ii) a decrease in cardiac performance of the heart; and altering the hemodynamic support applied based on determining whether cardiac performance of the heart is increasing or decreasing.

14. The method of claim 13, wherein the blood pump is an intracardiac blood pump that has a cannula configured to be positioned within a ventricle of the heart.

15. The method of claim 14, wherein the cannula is configured to be positioned within a left ventricle.

16. The method of claim 14, wherein a pressure sensor is provided with the intracardiac blood pump, and wherein detecting the plurality of aortic pressure measurements comprises measuring the aortic pressure via the pressure sensor.

17. The method of claim 16, wherein the pressure sensor is positioned within a housing of the blood pump.

18. The method of claim 14, wherein detecting the plurality of aortic pressure measurements comprises receiving the aortic pressure measurements from a pressure sensor separate from the intracardiac blood pump.

19. The method of claim 14, wherein operation of the intracardiac blood pump is adjusted by a controller, and wherein the controller comprises a memory storing the plurality of time dependent non-linear models of the vascular system.

20. The method of claim 1, further comprising displaying the determined cardiac output.

\* \* \* \* \*